(12) United States Patent
Odame

(10) Patent No.: US 8,655,438 B2
(45) Date of Patent: Feb. 18, 2014

(54) ELECTROENCEPHALOGRAPHY MONITORING DEVICE HAVING A SELF-ADAPTIVE ANALOG-TO-DIGITAL CONVERTER

(75) Inventor: Kofi Odame, Hanover, NH (US)

(73) Assignee: Dartmouth College, Hanover, NH (US)

( * ) Notice: Subject to any disclaimer, the term of this patent is extended or adjusted under 35 U.S.C. 154(b) by 327 days.

(21) Appl. No.: 12/711,348

(22) Filed: Feb. 24, 2010

(65) Prior Publication Data

US 2010/0217147 A1 Aug. 26, 2010

Related U.S. Application Data

(60) Provisional application No. 61/155,497, filed on Feb. 25, 2009.

(51) Int. Cl.
*A61B 5/04* (2006.01)
(52) U.S. Cl.
USPC .......................................... 600/544; 600/545
(58) Field of Classification Search
USPC ........................................................ 600/544
See application file for complete search history.

(56) References Cited

U.S. PATENT DOCUMENTS

| | | | |
|---|---|---|---|
| 4,800,895 A | 1/1989 | Moberg et al. | |
| 4,974,602 A | 12/1990 | Abraham-Fuchs et al. | |
| 5,226,424 A * | 7/1993 | Bible | 600/508 |
| 5,349,962 A | 9/1994 | Lockard et al. | |
| 6,016,449 A * | 1/2000 | Fischell et al. | 607/45 |
| 6,768,969 B1 | 7/2004 | Nikitin | |
| 7,478,108 B2 | 1/2009 | Townsend et al. | |
| 2007/0210951 A1* | 9/2007 | Yamaji | 341/156 |
| 2008/0146958 A1* | 6/2008 | Guillory et al. | 600/544 |
| 2008/0161713 A1* | 7/2008 | Leyde et al. | 600/544 |

\* cited by examiner

*Primary Examiner* — Michael Kahelin
*Assistant Examiner* — Yunqing Wang
(74) *Attorney, Agent, or Firm* — Peter A. Nieves; Sheehan Phinney Bass + Green PA

(57) ABSTRACT

An EEG monitoring device, contains at least one electrode, a non-linear analog signal processor, a variable resolution analog-to-digital converter, a storage, and a power source. The non-linear analog signal processor receives a signal from the at least one electrode and determines whether the signal is within a significant category. The variable resolution analog-to-digital converter converts signals received from the non-linear analog signal processor into high-resolution digital signals if the signals are within the significant category, and converts signals received from the non-linear analog signal processor at a low resolution if the signals are not within the significant category. The storage stores high-resolution digital signals received from the variable resolution analog-to-digital converter and the power source is connected to, and provides power to, the non-linear analog signal processor, the variable resolution analog-to-digital converter, and the storage.

19 Claims, 2 Drawing Sheets

ELECTROENCEPHALOGRAPHY MONITORING DEVICE HAVING A SELF-ADAPTIVE ANALOG-TO-DIGITAL CONVERTER

CROSS-REFERENCE TO RELATED APPLICATIONS

The present application claims priority to copending U.S. provisional patent application entitled "AN ELECTROENCEPHALOGRAPHY MONITORING DEVICE HAVING A SELF-ADAPTIVE ANALOG-TO-DIGITAL CONVERTER," having Ser. No. 61/155,497, filed Feb. 25, 2009, which is hereby incorporated herein by reference in its entirety.

FIELD OF THE INVENTION

The present invention relates to electroencephalography (EEG) monitoring devices, and specifically is related to an EEG monitoring device having a self-adaptive analog-to-digital converter.

BACKGROUND OF THE INVENTION

It is common practice for EEG information to be monitored and reviewed as a diagnostic tool, such as, for example, during cerebrovascular surgery. Typical EEG information is gathered from EEG monitoring devices. Unfortunately, typical EEG monitoring devices provide continuous analog-to-digital conversion of monitored signals and full-resolution due to use of a fixed resolution analog-to-digital converter. This results in wasteful conversion of monitored signals and the need for large amounts of storage space, especially since most monitored signals do not have medical significance. It is also unfortunate that the more storage being performed, the larger the size of storage device required, thereby resulting in EEG monitoring devices be fairly large in size.

It is also noted that typical EEG monitoring devices require large power supplies. This contributes to EEG monitoring devices not only being fairly large in size, but also heavy in weight.

Thus, a heretofore unaddressed need exists in the industry to address the aforementioned deficiencies and inadequacies.

SUMMARY OF THE INVENTION

The present system and method provides a lighter and more efficient electroencephalography (EEG) monitoring device. Briefly described, in architecture, one embodiment of the EEG monitoring device, among others, can be implemented as follows. The EEG monitoring device, contains at least one electrode, a non-linear analog signal processor, a variable resolution analog-to-digital converter, a storage, and a power source. The non-linear analog signal processor receives a signal from the at least one electrode and determines whether the signal is within a significant category. The variable resolution analog-to-digital converter converts signals received from the non-linear analog signal processor into high-resolution digital signals if the signals are within the significant category, and converts signals received from the non-linear analog signal processor at a low resolution if the signals are not within the significant category. The storage stores high-resolution digital signals received from the variable resolution analog-to-digital converter and the power source is connected to, and provides power to, the non-linear analog signal processor, the variable resolution analog-to-digital converter, and the storage.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

The present EEG monitoring device contains an analog-to-digital converter (ADC) for multiple channels of EEG signals. The ADC monitors the EEG signals and varies its conversion resolution depending on whether or not it has detected an event of clinical significance, such as, for example, an ictal episode. During clinically significant events, the resolution of the ADC is high to facilitate analysis by an expert clinician. It should be noted, however, that for the majority of the time, the resolution of the ADC remains low as a nonlinear analog signal processor monitors the EEG signals for the onset of an important event. It should be noted that in the EEG monitoring device the nonlinear analog signal processor is distinct from a (digital) microprocessor that occurs after the ADC in a signal processing chain, as shown by FIG. 1.

The ADC is intended for wearable and implantable EEG monitoring devices. By adopting its analog-to-digital conversion resolution accordingly, the volume of EEG information that is digitized, stored, and transmitted is reduced. This leads to a reduction in the power consumption and the data storage needs of wearable and implantable EEG monitoring devices. Therefore, the EEG monitoring devices can be small and can maintain a long battery life.

Figure 1:
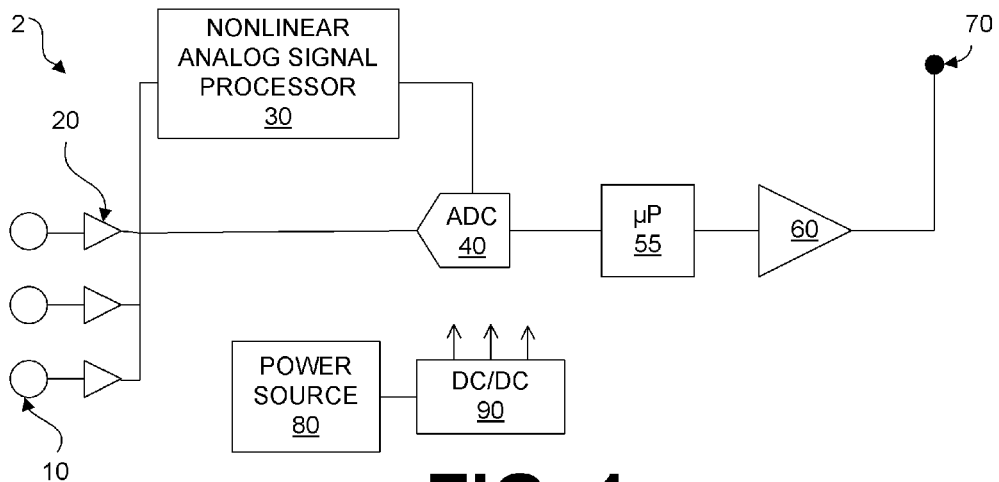
FIG. 1 is a block diagram illustrating an EEG monitoring device in accordance with the present invention.

FIG. 1 is a block diagram illustrating an EEG monitoring device in accordance with the present invention. As shown by FIG. 1, the EEG monitoring device 2 contains at least one electrode 10 connected to at least one amplifier 20. The electrodes are used to capture the EEG signals. As the EEG signal is of very small amplitude, it is susceptible to corruption by electrical noise and other external interferences. The amplifier increases the amplitude of the EEG signal such that it is not susceptible to corruption.

The amplifier 20 is connected to a non-linear analog signal processor 30, which is described in detail below. The non-linear analog signal processor 30 is connected to a variable resolution analog-to-digital converter (ADC) 40. The ADC 40 converts the amplified EEG signal to a digital signal. For EEG signals that are relevant to ictal episodes, the ADC 40 converts EEG signals at a high resolution. The high resolution is important for the clinician to do accurate analysis of the EEG signal. However, constant high resolution conversion would drain battery power. To conserve power, the ADC 40 converts EEG signals that are not relevant to ictal episodes at a much lower resolution.

The ADC 40 is connected to a microprocessor 55 having a memory (not shown). The microprocessor 55 collects the output of the ADC 40 and stores it in the memory. The memory is used as a buffer to hold digitized EEG data. Once this buffer is filled, the accumulated data is transmitted wirelessly. It should be noted that it is more power-efficient to periodically transmit large accumulations of data than to continuously transmit small amounts of data.

The microprocessor 55 and memory are connected to RF modulation circuitry and a driver 60. The modulation circuitry could implement any number of schemes for preparing the digital data for transmission. One commonly used modulation scheme in biomedical devices, such as this one, is frequency shift keying. The driver is a high-powered amplifier that outputs the modulated data to the antenna 70. The antenna 70 in response emits the data as radio-frequency waves. One having ordinary skill in the art would appreciate that data may instead be transmitted by a different means.

A power source 80 is located within the EEG monitoring device 2 and connects to all portions of the EEG monitoring device 2, except for the electrodes 10. In accordance with one embodiment of the invention, the power source may be a battery. The battery serves as a DC (Direct Current) power source and may be a primary or a rechargeable (secondary) type, may include a single or few batteries, and may use various chemicals for the electro-chemical cells. Commonly, the battery (or batteries) is enclosed in a battery compartment or a battery holder, allowing for easy replacement, such as in a battery compartment. A DC/DC converter 90 may be added between the battery and one or all the electrical circuits in the EEG monitoring device 2, adapting between the battery voltage and the voltage required by the internal electrical circuits. Alternatively, the power source 80 may be a permanent and non-removable power source, or the power source may require connection to a standard outlet for receiving power.

Figure 2:
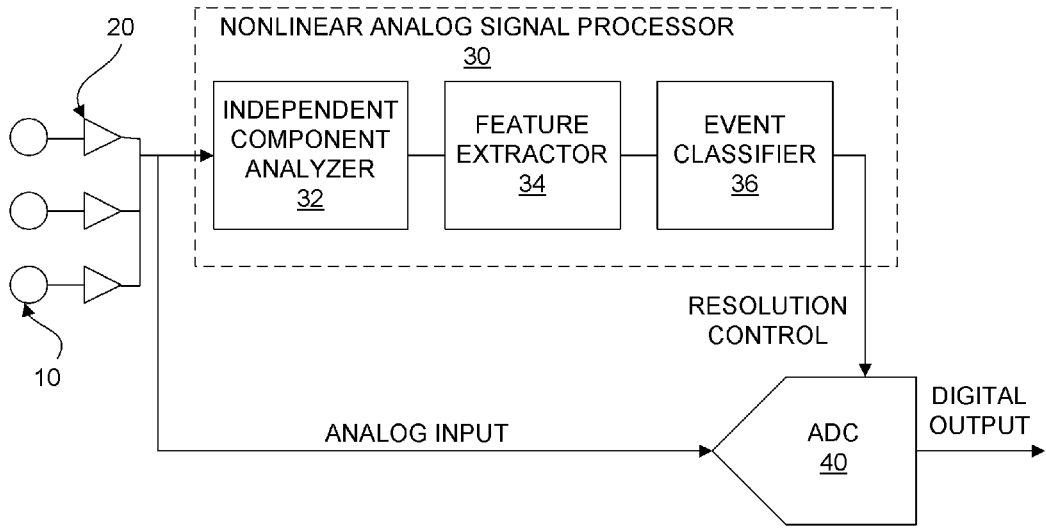
FIG. 2 is a block diagram further illustrating the non-linear analog signal processor of the EEG monitoring device and functionality performed by the processor.

FIG. 2 is a block diagram further illustrating the non-linear analog signal processor 30 of the EEG monitoring device 2 and functionality performed by the processor 30. As illustrated by FIG. 2, a signal fed from electrodes 10 is received by the nonlinear analog signal processor 30. The nonlinear analog signal processor 30 analyzes received EEG signals that are detected by the electrodes 10 and identifies whether the EEG signals are significant or not. In accordance with the present invention, a significant EEG signal is defined as one that indicates the occurrence of an ictal event.

The purpose of the nonlinear analog signal processor 30 is to perform preliminary analysis of the EEG signals before they are digitized by the variable resolution analog-to-digital converter 40. The result of this preliminary analysis determines the resolution at which digitization should occur.

The nonlinear analog signal processor 30 contains an independent component analyzer 32, a feature extractor 34, and an event classifier 36. It should be noted that the independent component analyzer 32, feature extractor 34, and event classifier 36 may be provided as hardware, software, or firmware.

The first steps in automated EEG analysis by the nonlinear analog signal processor 30 are used for filtering and blind source separation. The independent component analyzer 32 provides the blind source separation functionality. Since blind source separation is known by those having ordinary skill in the art, a detailed description of the same is not provided herein. As is known by those having ordinary skill in the art, blind source separation is the task of processing a mixture of signals so as to recover the constituent parts.

One example, among others, of an independent component analyzer 32 has been proposed by Christian Jutten and Jeanny Herault. Independent component analysis uses equations 1 and 2 below.

$$S_i = E_i - \Sigma c_{ij} S_j, j \neq i \qquad (Eq. 1)$$

$$dc_{ij}/dt = S_i^3 \tan h(S_j) \qquad (Eq. 2)$$

In equations 1 and 2, $E_i$ represents the signal that has been captured by the i'th electrode. This signal is a mixture of individual EEG signals. $S_i$ represents the output of the independent component analyzer 32, where $S_i$ is one of the constituent parts of the mixture $E_i$. The $c_{ij}$ terms are weighting terms that must be calculated via an adaptation rule, equation 2. In order to implement the adaptation rule, equation 2, in a power-efficient manner, the cubic term is replaced with a signum and a square term. Thus, the adaptation rule becomes as illustrated in equation 3 below.

$$dc_{ij}/dt = sgn(S_i) S_i^2 \tan h(S_j). \qquad (Eq. 3)$$

The squaring of $S_i$ can be achieved by making use of the V-I square-law of a transistor. The output of the squaring circuit is then used as the bias current of an operational-transconductance amplifier, whose non-inverting input is $S_j$. The signum term is implemented as a switch, turned on or off depending on the sign of $S_i$.

Having described the independent component analyzer 32, the following further describes the feature extractor 34. For monitoring of epilepsy patients, clinicians are most interested in analyzing the EEG data collected during a short period around a seizure episode. As an example, clinicians may be most interested in an 8-minute bracket around a seizure episode. That is, clinicians want EEG data that occurred 4 minutes before, during, and 4 minutes after a seizure, or until the seizure stops. It is therefore only necessary to perform high-resolution analog-to-digital conversion during this period of interest.

Figure 3:
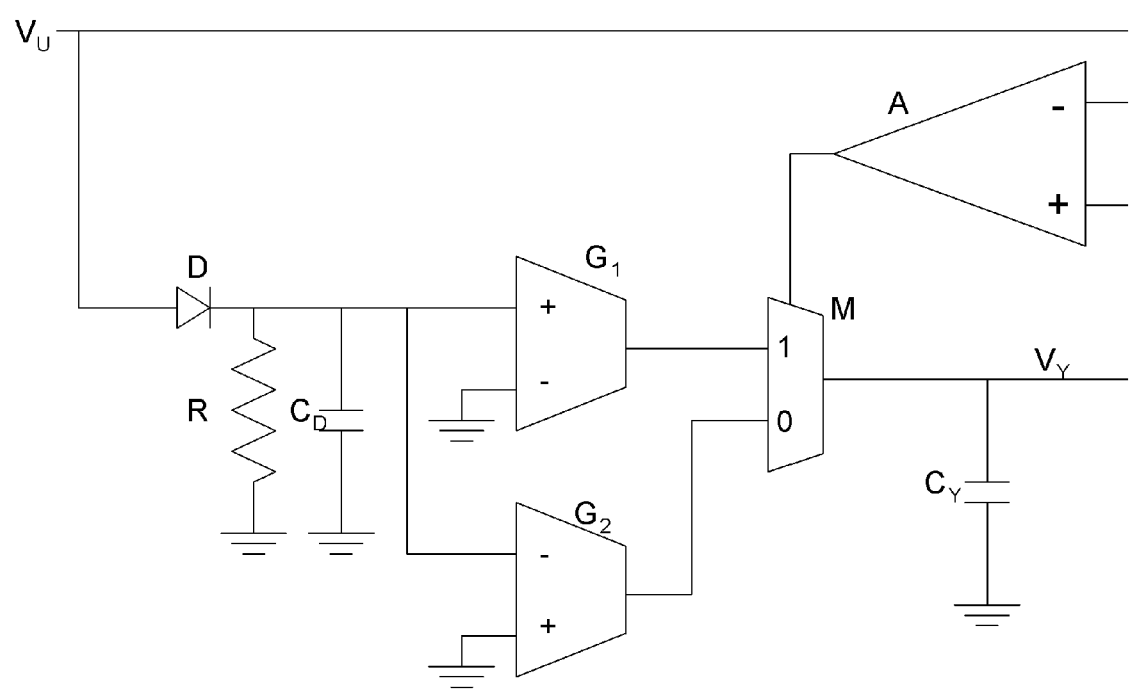
FIG. 3 is a schematic diagram illustrating an analog implementation of a feature extractor, which is significantly less complex and more power-efficient than prior extractors.

The onset of a seizure is marked by changes in the statistical properties of the EEG signals. As is known by those having ordinary skill in the art, the ratio of the median of the foreground EEG to that of a background reference increases as a seizure event is approached. FIG. 3 is a schematic diagram illustrating an analog implementation of a feature extractor, which is significantly less complex and more power-efficient than prior extractors. The feature extractor performs the functions illustrated by equation 4 below.

$$dy/dt = (p - H(y-u)) \max(u) \qquad (Eq. 4)$$

In equation 4, p is the target percentile, H is the Heaviside function, y is the output, and u is the input. It should be noted that other algorithms can similarly extract representative statistical features of the EEG signal that indicates the occurrence of a seizure event.

The diode D and the resistor R act as a half-wave rectifier to the input $V_U$. The capacitor $C_D$ holds the peak of the half-wave rectified signal. The voltage across the capacitor $C_D$ is effectively the peak, or maximum value of the input $V_U$. The maximum value of $V_U$ is applied to the inputs of the transconductance elements $G_1$ and $G_2$. The transconductance element $G_1$ outputs a current that is proportional to the maximum value of $V_U$. This output current, $I_{G1}$, is given by the expression of equation 5 below.

$$I_{G1}=(G_P-G_K)*\max(V_U) \quad \text{(Eq. 5)}$$

In equation 5, $G_P$ and $G_K$ are constants.

Similarly, the transconductance element $G_2$ outputs a current, $I_{G2}$. This output current is given by the expression of equation 6 below.

$$I_{G2}=G_P*\max(V_U). \quad \text{(Eq. 6)}$$

The comparator A outputs a digital logic '1' if the magnitude of $V_U$ is greater than that of $V_Y$. It outputs a digital logic '0' otherwise. The output of the comparator A is the control input of the current-mode multiplexer, M. That is, the output, $A_{out}$, of the comparator A, is given as shown by equation 7 below.

$$A_{out}=H(V_Y-V_U), \quad \text{(Eq. 7)}$$

In equation 7, H is the Heaviside operator.

The current-mode multiplexer M outputs a current that is equal to one of its input currents, depending on the digital logic value of its control input. If its control input is a digital logic '1', then the output of the multiplexer M is $I_{G1}$. If its control input is a digital logic '0', then the output of the multiplexer M is $I_{G2}$. Since its control input is governed by equation 7, the output current, $I_M$, of multiplexer M, is given as shown by equation 8 below.

$$I_M=(G_P-G_K*H(V_Y-V_U))*\max(V_U) \quad \text{(Eq. 8)}$$

According to Kirchhoff's current law, the output current $I_M$ must be equal to the current that flows through capacitor $C_Y$. Mathematically, $$C_Y dV_Y/dt=I_M \quad \text{(Eq. 9)}$$

Further, from equation 8, we can write equation 10, below.

$$C_Y dV_Y/dt=(G_P-G_K*H(V_Y-V_U))*\max(V_U) \quad \text{(Eq. 10)}$$

One skilled in the art would recognize that equation 10 is analogous to equation 4

Returning to FIG. 2, the event classifier 36 is a neural network that can be trained either on patient-specific data, or on the data of a patient population. Those with ordinary skill in the art would know how to train a neural network. Once trained, the neural network will be able to discriminate between features that are indicative of a seizure event and those that are not.

Sampling and quantization are the two components of any conventional ADC. "Resolution control" is a control signal that changes the resolution of the quantizer of the ADC 40, depending on if an event of interest has been detected. The "analog input" to the ADC 40 is the EEG signal, still in raw analog form. The "digital output" of FIG. 2 is the digitized version of the EEG signal, which is the output of the ADC 40.

If no event of clinical significance is detected, the EEG signals are converted to low-resolution digital samples by the ADC 40. These low-resolution digital samples are stored by the microprocessor in its buffer. Eventually, buffered digital samples are discarded, to make room for newly-arriving digital samples. If an important event is detected, the EEG signals are converted to high-resolution digital samples by the ADC 40. The microprocessor stores the high-resolution data in its circular buffer for the next short time period, as an example, but not limited to, for the next four minutes. The microprocessor then outputs this data to the RF modulation circuitry, which transmits the data wirelessly via the driver amplifier and antenna 70. The data is received by a wireless receiver and is made available to the clinician.

It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

I claim:

1. An electroencephalography (EEG) monitoring device, comprising:
    at least one electrode;
    a non-linear analog signal processor configured to receive a signal from the at least one electrode and determine whether the signal is within a significant category, wherein a significant EEG event is within the significant category, the non-linear analog signal processor comprising:
        an independent component analyzer configured to provide blind source separation functionality at least in part by implementing an adaptation rule as a product of a sign of a first processed signal from a first electrode, a square of the first processed signal, and a hyperbolic tangent of a second processed signal; and
        a feature extractor for extracting representative statistical features of an EEG signal configured to indicate occurrence of a seizure event;
    a variable resolution analog-to-digital converter configured to convert signals received from the non-linear analog signal processor into high-resolution digital signals if the signals are within the significant category, and configured to convert signals received from the non-linear analog signal processor at a low resolution if the signals are not within the significant category;
    storage means configured to store high-resolution digital signals received from the variable resolution analog-to-digital converter; and
    a power source connected to, and providing power to, the non-linear analog signal processor, the variable resolution analog-to-digital converter, and the storage means.

2. The EEG monitoring device of claim 1 further comprising at least one amplifier connected to the at least one electrode and configured to amplify a signal received from the at least one electrode.

3. The EEG monitoring device of claim 1, further comprising RF modulation circuitry and a driver configured to receive at least one of a high-resolution digital signal and a low-resolution digital signal from the variable resolution analog-to-digital converter.

4. The EEG monitoring device of claim 3, further comprising an antenna connected to said driver.

5. The EEG monitoring device of claim 1, wherein a signal within the significant category represents an ictal episode.

6. The EEG monitoring device of claim 1, wherein the low-resolution digital samples are not stored within the storage means.

7. The EEG monitoring device of claim 1, wherein the storage means is a memory.

8. The EEG monitoring device of claim 1, wherein the storage means is a memory located within a microprocessor.

9. The EEG monitoring device of claim 8, wherein the memory is configured to store the high-resolution digital signals until filled, after which the microprocessor is configured to transmit the high-resolution digital signals wirelessly.

10. The EEG monitoring device of claim 1, wherein the power source is a removable battery.

11. The EEG monitoring device of claim 1, wherein the non-linear analog signal processor further comprises an event classifier configured to be trained either on patient-specific data, or on data of a patient population.

12. The EEG monitoring device of claim 1, wherein the independent component analyzer comprises a squaring circuit comprising a V-I square law of a transistor.

13. The EEG monitoring device of claim 12, wherein an output of the squaring circuit is used as a bias current of an operational-transconductance amplifier whose non-inverting input is the second signal.

14. The EEG monitoring device of claim 1, wherein the independent component analyzer comprises a switch configured to turn on or off depending on the sign of the first signal.

15. An electroencephalography (EEG) monitoring device, comprising:
    at least one electrode;
    a non-linear analog signal processor configured to receive a signal from the at least one electrode and determine whether the signal is within a significant category, wherein a significant EEG event is within the significant category, the non-linear analog signal processor comprising:
        an independent component analyzer configured to provide blind source separation functionality; and
        a feature extractor for extracting representative statistical features of an EEG signal configured to indicate occurrence of a seizure event at least in part by
            applying a peak value of an input signal to a first transconductance element and a second transconductance element, and
            with a multiplexer, multiplexing the outputs of the first transconductance element and the second transconductance element according to a comparator configured to compare the input signal to the output signal,
            wherein the output signal comprises the output of the multiplexer.
    a variable resolution analog-to-digital converter configured to convert signals received from the non-linear analog signal processor into high-resolution digital signals if the signals are within the significant category, and configured to convert signals received from the non-linear analog signal processor at a low resolution if the signals are not within the significant category;
    storage means configured to store high-resolution digital signals received from the variable resolution analog-to-digital converter; and
    a power source connected to, and providing power to, the non-linear analog signal processor, the variable resolution analog-to-digital converter, and the storage means.

16. The EEG monitoring device of claim 15, wherein the comparator is configured to approximate a heavyside operator.

17. The EEG monitoring device of claim 15, wherein the peak value of the input signal comprises the output of circuitry comprising a half-wave rectifier and a capacitor.

18. The EEG monitoring device of claim 15, wherein the input signal comprises an output of the independent component analyzer.

19. The EEG monitoring device of claim 15, wherein the multiplexer comprises a current-mode multiplexer.

* * * * *